United States Patent
Hong et al.

(10) Patent No.: US 12,254,535 B2
(45) Date of Patent: Mar. 18, 2025

(54) TIME AND POSITION BASED BINNING OF IMAGE DATA

(71) Applicant: Siemens Medical Solutions USA, Inc., Malvern, PA (US)

(72) Inventors: Inki Hong, Knoxville, TN (US); Ziad Burbar, Knoxville, TN (US); Paul Schleyer, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 566 days.

(21) Appl. No.: 17/597,658

(22) PCT Filed: Oct. 10, 2019

(86) PCT No.: PCT/US2019/055510
§ 371 (c)(1),
(2) Date: Jan. 17, 2022

(87) PCT Pub. No.: WO2021/071487
PCT Pub. Date: Apr. 15, 2021

(65) Prior Publication Data
US 2022/0262048 A1   Aug. 18, 2022

(51) Int. Cl.
*G06T 11/00* (2006.01)
*A61B 6/00* (2024.01)

(52) U.S. Cl.
CPC .......... *G06T 11/005* (2013.01); *A61B 6/5264* (2013.01); *G06T 2211/412* (2013.01)

(58) Field of Classification Search
CPC .......... G06T 11/005; G06T 2210/41
See application file for complete search history.

(56) References Cited

U.S. PATENT DOCUMENTS

2014/0119611 A1 * 5/2014 Prevrhal ............... G06T 11/005
382/107
2015/0051713 A1 * 2/2015 Azvine .................. H04H 60/45
700/1

(Continued)

FOREIGN PATENT DOCUMENTS

| CN | 109009199 | 12/2018 |
|---|---|---|
| WO | 2018172229 | 9/2018 |
| WO | 2018172566 | 9/2018 |

OTHER PUBLICATIONS

Defrise et al., Continuous and discrete data rebinning in time-of-flight PET, IEEE Trans Med Imaging. Sep. 2008;27(9), pp. 1310-1322, doi: 10.1109/TMI.2008.922688. PMID: 18779067.*

(Continued)

*Primary Examiner* — Guillermo M Rivera-Martinez (57) ABSTRACT

A system and method include association of imaging event data to one of a plurality of bins based on a time associated with the imaging event data, determination that the time periods of a first bin and the time periods of a second bin are adjacent-in-time, determination of whether a spatial characteristic of the imaging event data of the first bin is within a predetermined threshold of the spatial characteristic of the imaging event data of the second bin, and, based on the determination, reconstruction of one or more images based on the imaging event data of the first bin and the second bin.

18 Claims, 8 Drawing Sheets

(56) References Cited

U.S. PATENT DOCUMENTS

| | | | |
|---|---|---|---|
| 2016/0253826 A9* | 9/2016 | Ziv | A61B 5/418 382/131 |
| 2016/0371849 A1* | 12/2016 | Pavek | G06T 7/20 |
| 2021/0090215 A1* | 3/2021 | Ben-Haim | G06T 7/55 |

OTHER PUBLICATIONS

Defrise et al., Exact and approximate rebinning algorithms for 3-D PET data, IEEE Trans Med Imaging, Apr. 1997;16(2), pp. 145-158, doi: 10.1109/42.563660. PMID: 9101324.*

Lu et al., Data-driven voluntary body motion detection and non-rigid event-by-event correction for static and dynamic PET, hys Med Biol. Mar. 8, 2019;64(6), pp. 1-13 065002. doi: 10.1088/1361-6560/a, AAPA furnished vis IDS.*

Yihuan Lu et al: "Data-driven voluntary body motion detection and non-rigid event-by-event correction for static and dynamic PET", Physics in Medicine and Biology, vol. 64, No. 6, Mar. 8, 2019 (Mar. 8, 2019).

International Search Report for Corresponding PCT Application No. PCT/US2019/055510, dated Oct. 10, 2019.

* cited by examiner

TIME AND POSITION BASED BINNING OF IMAGE DATA

BACKGROUND

According to conventional nuclear imaging, a radiopharmaceutical is introduced into a patient body by injection or ingestion. The radiopharmaceutical emits gamma rays (in the case of single-photon-emission-computer-tomography (SPECT) imaging) or positrons which annihilate with electrons to produce gamma rays (in the case of positron-emission-tomography (PET) imaging). A detector system located outside the body detects the emitted gamma rays and reconstructs images based thereon.

Detection of the emitted gamma rays occurs over a period of time, during which the body may move, either by inadvertently or due to natural physiological processes such as respiration and heartbeat. Such movement can lead to blurred images, particularly in the head, abdominal, thoracic and cardiac regions.

Some systems address the foregoing by constraining the imaged volume. Other systems detect patient movement using external hardware such as a three-dimensional camera. The movement may be recorded as motion vectors occurring at particular times during the data acquisition. The motion vectors are then used to determine periods of no or relatively low motion (i.e., motion frames), and to correct data acquired between the motion frames to account for the inter-frame motion.

An image may be reconstructed from the corrected data. Data acquired during a period of relatively significant motion is discarded and is not used for image reconstruction. This data loss may adversely affect the quality of the reconstructed image.

Systems are desired to identify motion frames based on imaging data alone, and which preserve a larger portion of acquired data for image reconstruction than other motion-correction systems.

DETAILED DESCRIPTION

The following description is provided to enable any person in the art to make and use the described embodiments and sets forth the best mode contemplated for carrying out the described embodiments. Various modifications, however, will remain apparent to those in the art.

Generally, some embodiments determine clusters of event data which are acquired during a period of no or low subject motion. The event data of a given cluster may therefore be used to reconstruct an image with minimal motion artifacts.

Each cluster is associated with an acquisition time window and spatial information determined based on the event data within the cluster. Motion between temporally-adjacent clusters may be determined based on the spatial information of the temporally-adjacent clusters. The determined motion may be used for subsequent motion-correction of clustered event data, prior to or during image reconstruction.

Advantageously, the clusters may be determined without additional monitoring data provided by a motion detection system such as an external 3D camera. Some embodiments also provide clustering of temporally-adjacent event data, as opposed to data clustering techniques (e.g., k-means clustering) which fail to consider temporal associations between the data.

Figure 1:
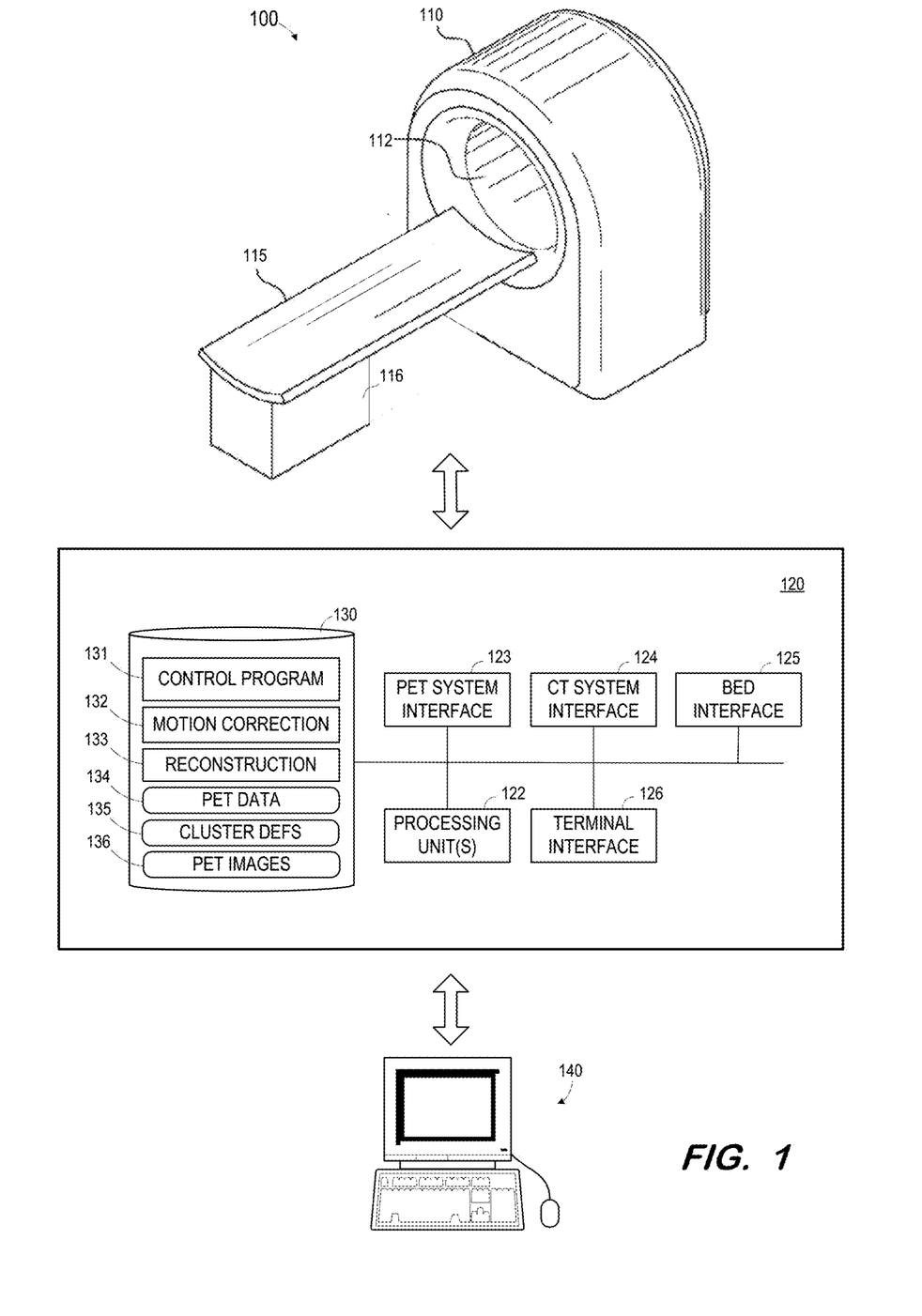
FIG. 1 is a block diagram of a PET/CT imaging system according to some embodiments.

FIG. 1 illustrates PET/CT system 100 to execute one or more of the processes described herein. Embodiments are not limited to system 100. In particular, although the acquired data described herein is referred to as event data (i.e., corresponding to gamma ray detections), embodiments are not limited to SPECT and PET imaging systems. For example, embodiments may be applied to data acquired by Computed Tomography (CT), Magnetic Resonance (MR), ultrasound or other imaging modalities, so long as the acquired data are associated with an acquisition time and a three-dimensional position.

System 100 includes gantry 110 defining bore 112. As is known in the art, gantry 110 houses PET imaging components for acquiring PET image data and CT imaging components for acquiring CT image data. The PET imaging components may include any number of gamma cameras in any configuration as is known in the art. The CT imaging components may include one or more x-ray tubes and one or more corresponding x-ray detectors.

According to conventional PET imaging, a tracer compound including a radionuclide is introduced into a patient body by injection or ingestion. Radioactive decay of the radionuclide generates positrons, which eventually encounter electrons and are annihilated thereby. Annihilation produces two gamma photons which travel in approximately opposite directions. Accordingly, an annihilation event is identified when two detectors disposed on opposite sides of the body detect the arrival of two oppositely-travelling gamma photons within a particular coincidence time window.

Because the two gamma photons travel in approximately opposite directions, the locations of the two detectors determine a Line-of-Response (LOR) along which the annihilation event occurred. Time-of-flight (TOF) PET measures the difference between the detection times of the two gamma photons arising from the annihilation event. This difference may be used to estimate a particular position along the LOR at which the annihilation event occurred. Accordingly, each annihilation event may be represented by raw (i.e., list-mode) data specifying the three-dimensional position and the time at which the event occurred.

Bed 115 and base 116 are operable to move a patient lying on bed 115 into and out of bore 112. In some embodiments, bed 115 is configured to translate over base 116 and, in other embodiments, base 116 is movable along with or alternatively from bed 115.

Movement of a patient into and out of bore 112 may allow scanning of the patient using the CT imaging elements and the PET imaging elements of gantry 110. Such scanning may proceed based on scanning parameters such as scan ranges and corresponding scanning speeds. Bed 115 and base 116 may provide continuous bed motion, as opposed to step-and-shoot motion, during such scanning according to some embodiments.

Control system 120 may comprise any general-purpose or dedicated computing system. Accordingly, control system 120 includes one or more processing units 122 configured to execute processor-executable program code to cause system 120 to operate as described herein, and storage device 130 for storing the program code. Storage device 130 may comprise one or more fixed disks, solid-state random-access memory, and/or removable media (e.g., a thumb drive) mounted in a corresponding interface (e.g., a USB port).

Storage device 130 stores program code of control program 131. One or more processing units 122 may execute control program 131 to, in conjunction with PET system interface 123, bed interface 125, and monitor interface 127, control hardware elements to move a patient into bore 112 and, during the movement, control gamma cameras to rotate around bore 112 and to detect coincidence events occurring within a body located in bore 112. The detected events may be stored in memory 130 as PET data 134, which may comprise list-mode data and/or sinograms.

One or more processing units 122 may also execute control program 131 to, in conjunction with CT system interface 124, cause a radiation source within gantry 110 to emit radiation toward a body within bore 112 from different projection angles, and to control a corresponding detector to acquire two-dimensional CT data. The CT data may be acquired substantially contemporaneously with the PET data as described above, and may be stored as CT data 136.

Storage device 130 also includes motion correction program 132 for correcting acquired PET data based on motion information. For example, embodiments may determine a motion vector representing patient motion between a first time period and a second time period. Motion correction program 132 may be executed to correct PET data acquired during the second time period based on the motion vector, such that the corrected data is registered with PET data acquired during the first time period.

Cluster definitions 135 specify time ranges and spatial information corresponding to each of several clusters of event data. The time range of a cluster indicates the event data associated with the cluster (i.e., the event data acquired during the time range). The spatial information corresponding to each cluster may be used to determine motion vectors between clusters. Generation of cluster definitions 135 according to some embodiments will be described in detail below.

Reconstruction program 133 may be executed to reconstruct PET images from PET data 134 using any reconstruction algorithm that is or becomes known. As will be described below, two or more PET images may be reconstructed from respective clusters of event data acquired during no- or low-motion time periods, and/or a single PET image may be reconstructed from the event data of all clusters which has been corrected based on one or more inter-cluster motion vectors. Such PET images may be stored among PET images 136.

PET images and CT images may be transmitted to terminal 140 via terminal interface 126. Terminal 140 may comprise a display device and an input device coupled to system 120. Terminal 140 may display PET images, CT images, cluster definitions, and/or any other suitable images or data. Terminal 140 may receive user input for controlling display of the data, operation of system 100, and/or the processing described herein. In some embodiments, terminal 140 is a separate computing device such as, but not limited to, a desktop computer, a laptop computer, a tablet computer, and a smartphone.

Each component of system 100 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Figure 2:
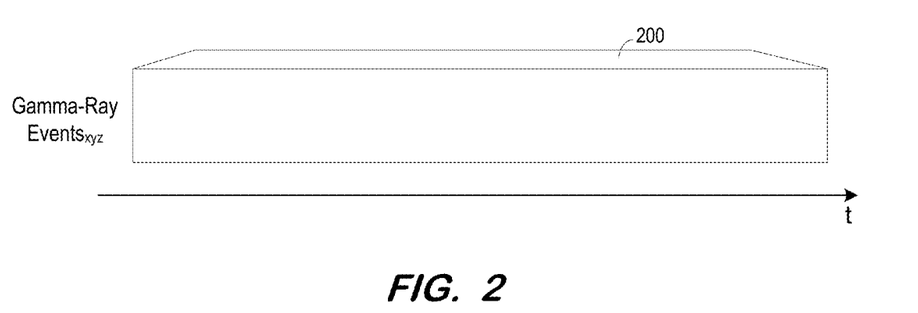
FIG. 2 illustrates event data acquired over time according to some embodiments.

FIG. 2 represents acquired event data 200 for purposes of describing some embodiments. Event data 200 describes events detected by a PET or SPECT scanner. Each event is described by an event time (i.e., the time at which the event occurred) denoted by its position along axis t, and a three-dimensional event position represented by the three-dimensional graphic of FIG. 2. The event position may be represented using any suitable coordinate system such as but not limited to a coordinate system of imaging system 100. Event data 200 may be acquired in list-mode as is known in the art.

Figure 3:
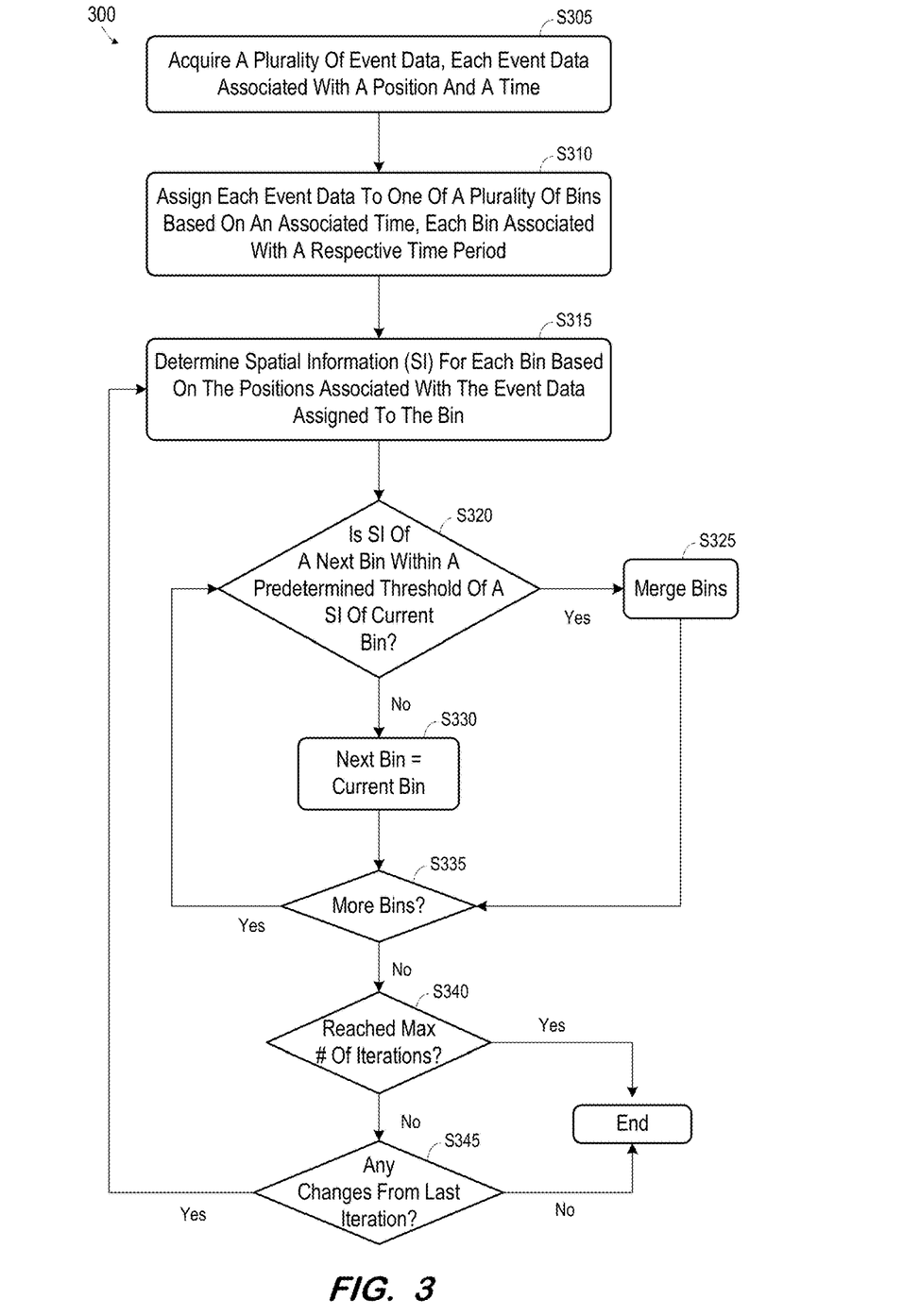
FIG. 3 comprises a flow diagram of a process to define motion frames based on event data according to some embodiments.

FIG. 3 comprises a flow diagram of process 300 to define motion frames based on event data according to some embodiments. Flow diagram 300 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape. Embodiments are not limited to the examples described below.

Initially, a plurality of event data is acquired at S305. The acquired event data may comprise, in some embodiments, list-mode PET data as described above. The event data may be acquired by an imaging system separate from a system to perform the remainder of process 300. The event data may be originally acquired in an imaging theatre, with process 300 being executed hours, days, months, etc. after the acquisition. Moreover, although the acquired data is described as event data, any data associated with an acquisition time and position may be acquired at S305.

Figure 4:
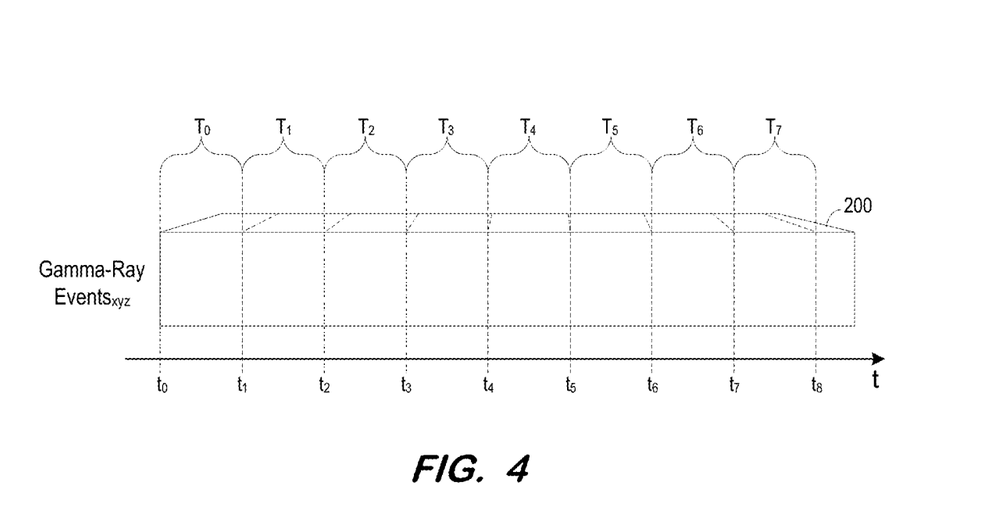
FIG. 4 illustrates time-based binning of event data according to some embodiments.

Next, at S310, each event data is assigned to (i.e., associated with) one of a plurality of bins. Each of the plurality of bins is associated with a time period, and the data of one event is assigned to a particular bin that is associated with a time period including the time of the one event. FIG. 4 illustrates bin assignment at S310 according to some embodiments, with respect to event data 200 of FIG. 2.

FIG. 4 shows eight bins $T_0$-$T_7$ including respective portions of data 200. Bin $T_0$ includes all event data acquired between time $t_0$ and $t_1$, bin $T_1$ includes all event data acquired between time $t_1$ and $t_2$, etc. In some embodiments, each bin represents a is time period, and hundreds of bins may be used. Embodiments are not limited to any bin duration or number of bins.

Spatial information (SI) associated with each bin is determined at S315. The determination is based on positions associated with the event data assigned to each bin. In one non-exhaustive example, S315 comprises determination of a spatial position associated with bin $T_0$ based on the positions associated with each event data assigned to bin $T_0$. In this regard, each event data of bin $T_0$ is associated with a three-dimensional position. Accordingly, the spatial position determined at S315 is a three-dimensional position around which the positions of each event data of bin $T_0$ are equally distributed. The determination at S315 may employ any suitable algorithm that is or becomes known.

Figure 5:
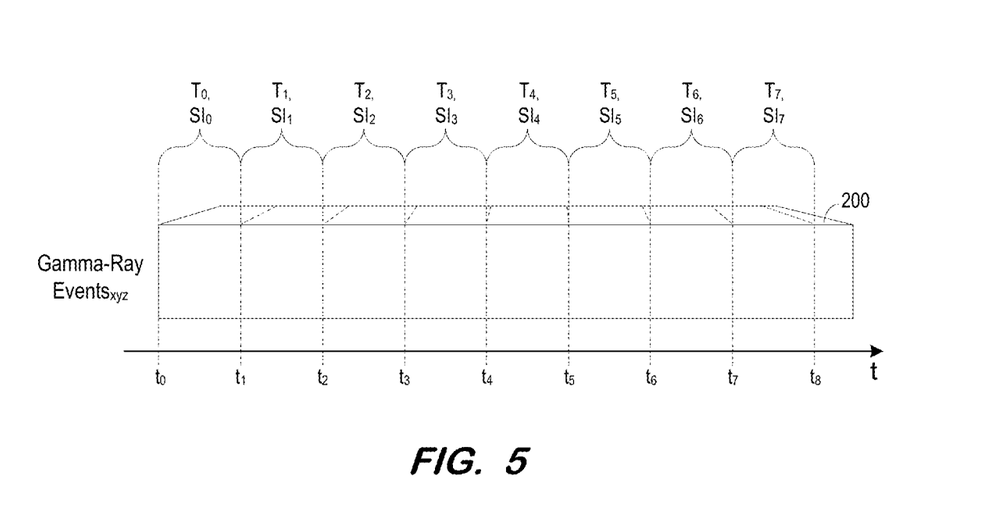
FIG. 5 illustrates determination of spatial information for each time-based bin of event data according to some embodiments.

FIG. 5 represents bins $T_0$-$T_7$ after determination of respective SIs according to some embodiments. As shown, bin $T_0$ is associated with $SI_0$, bin $T_1$ is associated with $SI_1$, etc. S315 may comprise the determination of any spatial characteristic or characteristics associated with each bin. The characteristic may be a representative position other than a geometric center of distribution. As will be evident from the description below, the SI determined for each bin at S315 may comprise a value/vector/equation representing a spatial entity that allows identification and quantification of motion between sets of event data.

Merging of the bins into clusters begins at S320. S320 includes a determination of whether the SI of a "next" bin is within a predetermined threshold of the SI of a "current" bin. At first execution, the determination at S320 assumes that a first-in-time bin (i.e., bin $T_0$) is a "current" bin.

The predetermined threshold may comprise a scalar value in some embodiments. Accordingly, the determination at S320 may comprise determining the distance between a three-dimensional coordinate (or line) of $SI_0$ and a three-dimensional coordinate (or line) of $SI_1$, and determining if the distance is less than the scalar value. Any other measures of spatial distance may be utilized at S320, depending upon the nature of the determined SI. If the SI of a bin is represented by a curve or other multi-point entity, S320 may comprise any suitable determination of distance between two such entities.

Figure 6:
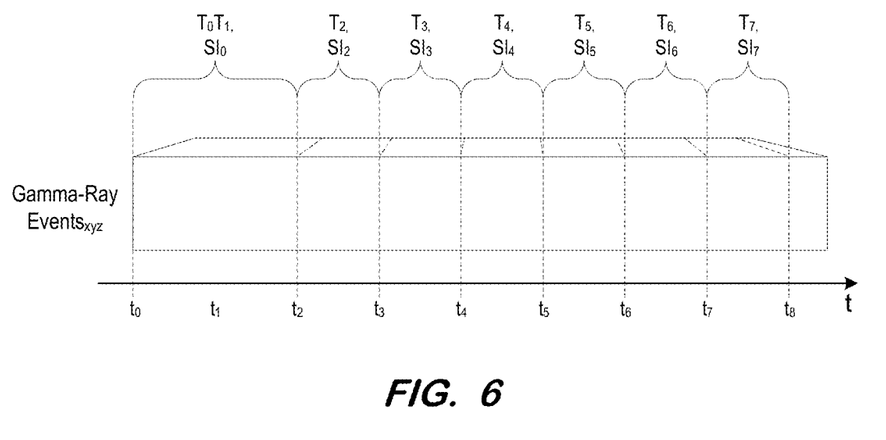
FIG. 6 illustrates merging of two time-based bins of event data according to some embodiments.

Flow proceeds to S325 if the determination at S320 is positive. The current and next bins are merged into a composite bin at S325. FIG. 6 illustrates merging of bins $T_0$ and $T_1$ according to some embodiments. The merged (i.e., composite) bin is labeled $T_0T_1$. Merging of the bins at S325 consists of assigning all of the event data of original bins $T_0$ and $T_1$ to the merged bin $T_0T_1$. As illustrated, the time period associated with merged bin $T_0T_1$ is $t_0$-$t_2$. Accordingly, the event data of merged bin $T_0T_1$ includes all event data associated with a time between $t_0$ and $t_2$.

Merged bin $T_0T_1$ is associated with $SI_0$. This association is used to ensure that any other bins merged with bin $T_0T_1$ are associated with SIs within the predetermined threshold of $SI_0$.

Figure 7:
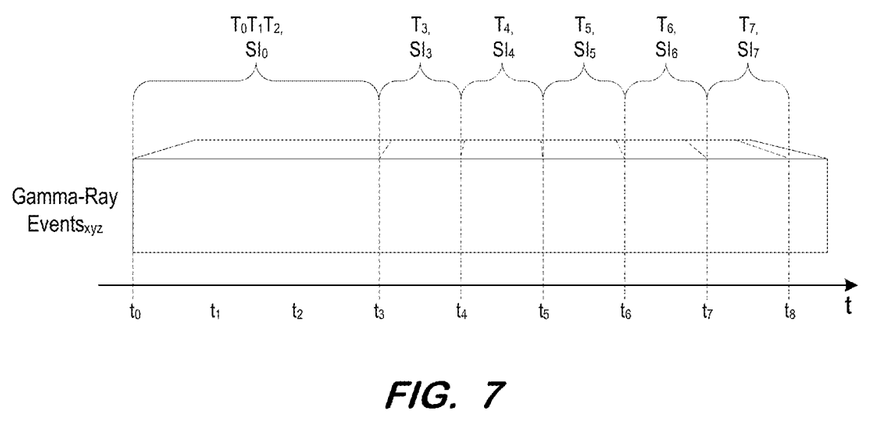
FIG. 7 illustrates merging of a third time-based bin of event data according to some embodiments.

Flow then continues to S335 to determine if another bin follows the "next" bin. In the present example, since bin $T_2$ follows bin $T_1$ in time, the determination at S335 is positive and flow returns to S320. $SI_2$ of next bin $T_2$ is compared with $SI_0$ of bin $T_0T_1$ at S320. It will be assumed that the $SI_2$ is within the predetermined threshold of $SI_0$ and therefore bin $T_2$ is merged with bin $T_0T_1$ at S325. FIG. 7 illustrates such a merging, in which merged bin $T_0T_1T_2$ includes all of the event data of original bins $T_0$, $T_1$ and $T_2$ and is associated with $SI_0$ and the time period $t_0$-$t_3$.

Since bin $T_3$ follows bin $T_2$ in time, flow proceeds from S325 through S335 and back to S320 as described above. It will be assumed that $SI_3$ of bin $T_3$ is not within the predetermined threshold of $SI_0$. Flow therefore continues to S330 to assign the next bin (i.e., bin $T_3$) as the current bin at S330. Due to the existence of next bin $T_4$, flow then returns to S320 to determine whether $SI_4$ of next bin $T_4$ is within the predetermined threshold of $SI_3$ of new "current" bin $T_3$.

Figure 8:
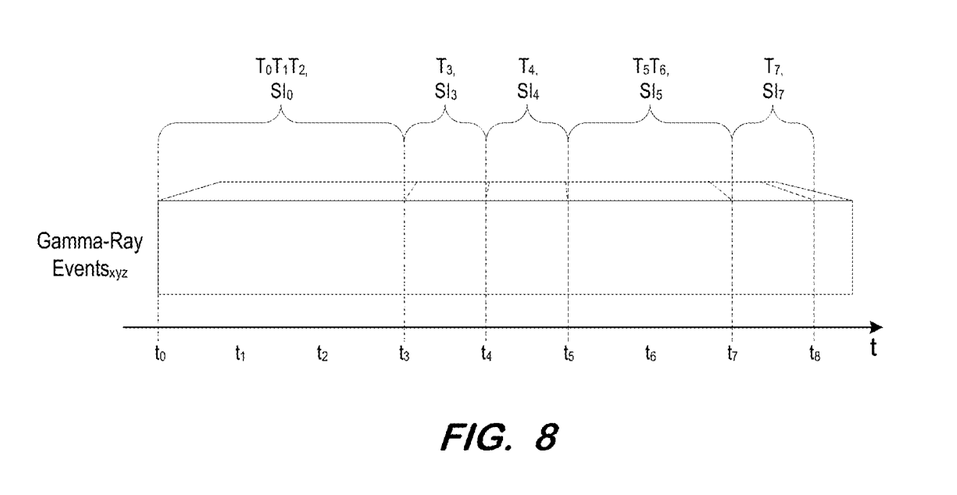
FIG. 8 illustrates merging of two time-based bins of event data according to some embodiments.

Process 300 continues as described above until it is determined at S335 that no "next" bin is available to evaluate against the current bin. As shown in FIG. 8, process 300 has executed to not merge bins $T_3$ and $T_4$, to not merge bins $T_4$ and $T_5$, to merge bins $T_5$ and $T_6$, and to not merge bins $T_5T_6$ and $T_7$.

Once it is determined at S335 that no "next" bin is available to evaluate against the current bin, it is determined at S340 whether a maximum number of iterations has been reached. The above description of S315 through S335 constitutes one iteration. Some embodiments may implement a pre-defined maximum number of such iterations. Flow terminate if it is determined that the maximum number of iterations has been reached.

Flow continues to S345 if it is determined at S375 that the maximum number of iterations has not been reached. At S345, it is determined whether the bins as defined at the end of the most-recently completed iteration are different from the bins as defined at the end of the immediately-prior iteration (i.e., did the last iteration change the bins?). If not, it is assumed that further iterations will not change the bins and flow terminates.

Figure 9:
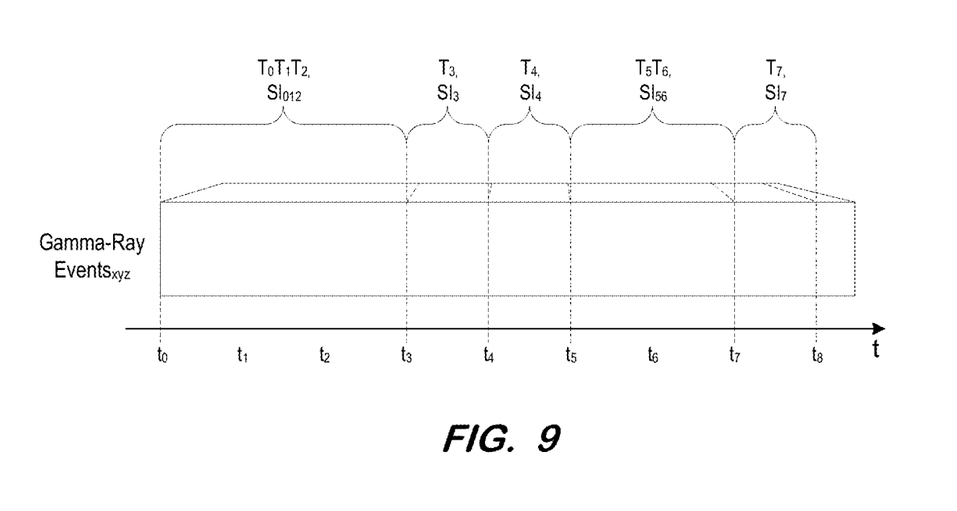
FIG. 9 illustrates clusters of event data and corresponding spatial information according to some embodiments.

Flow returns to S315 if the determination at S345 is positive, to determine SI associated with each currently-defined bin (i.e., bins $T_0T_1T_2$, $T_3$, $T_4$, $T_5T_6$ and $T_7$). FIG. 9 illustrates such spatial information for each of bins $T_0T_1T_2$, $T_3$, $T_4$, $T_5T_6$ and $T_7$. $SI_{012}$ of bin $T_0T_1T_2$ may differ from prior $SI_0$ due to its being determined based on the event data of each of prior bins $T_0$, $T_1$ and $T_2$. Similarly, $SI_{56}$ of bin $T_5T_6$ may differ from prior $SI_5$ due to its being determined based on the event data of each of prior bins $T_5$ and $T_5$.

Flow proceeds to S320 as described above to determine whether the SI of a next-in-time bin (e.g., $SI_3$ of bin $T_3$) is within a predetermined threshold of a SI of a current bin (e.g., $SI_{012}$ of cluster $T_0T_1T_2$). In some embodiments, each iteration uses a different predetermined threshold. Flow then continues as described above to merge bins whenever the determination at S320 is positive.

As mentioned above, the iterations continue until the maximum number of iterations has been executed or the bins were not changed by a last iteration. At the conclusion of process 300, the existing bins may be referred to as clusters. Each cluster is associated with a time period, event data of events which occurred during that time period, and spatial information determined based on the event data. Because the event data of each cluster occurred prior to all of the events of a next-in-time cluster, the SIs may be used to determine motion vectors between successive clusters. The motion vectors may then be used to motion-correct the event data prior to reconstruction. According to some embodiments, a cluster which is associated with a time period shorter than a given threshold is ignored during subsequent processing, as such a cluster is assumed to be associated with a period of significant motion.

Figure 10:
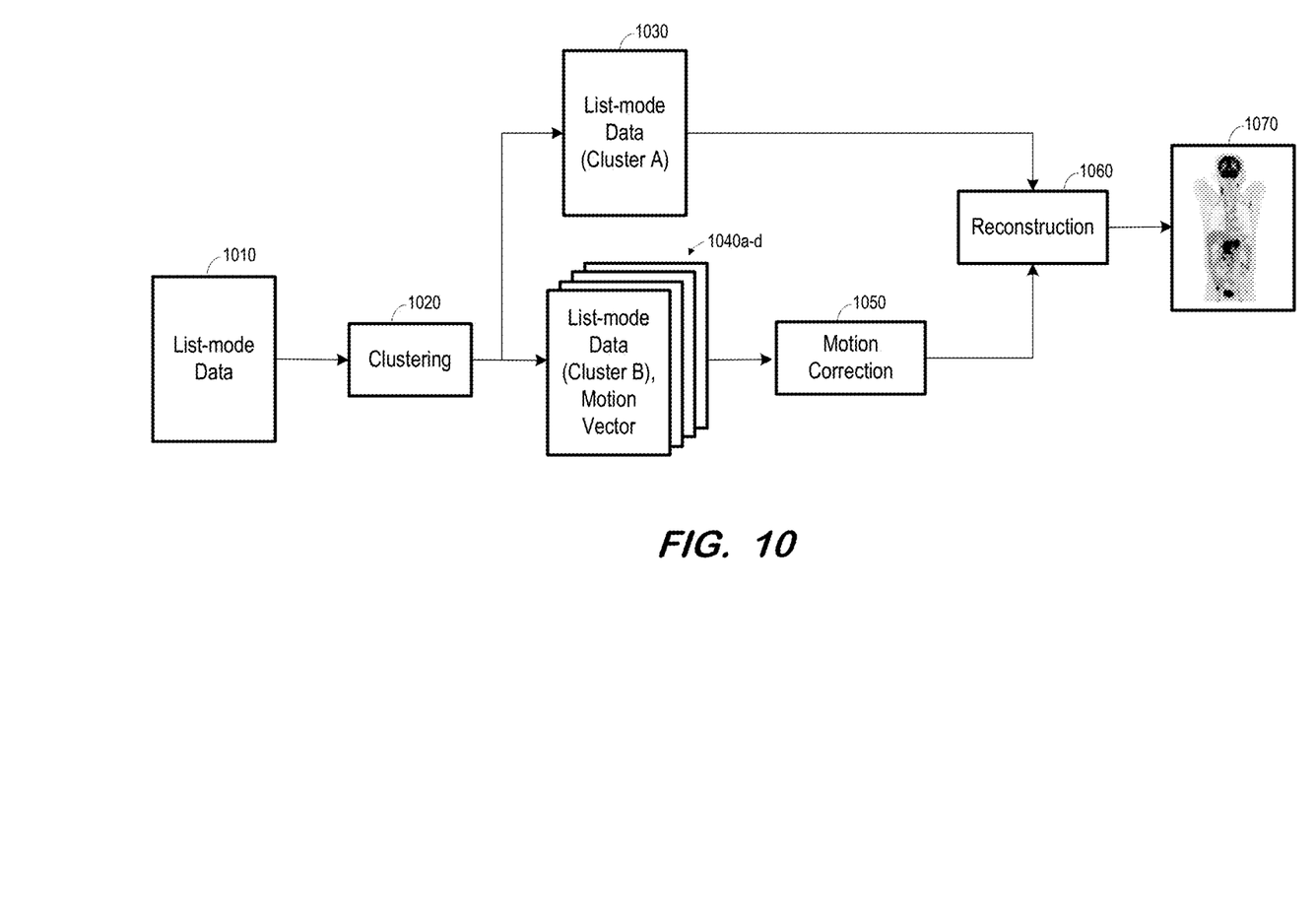
FIG. 10 illustrates a system for clustering, motion-correcting and reconstructing event data according to some embodiments.

FIG. 10 illustrates clustering, motion-correcting and reconstructing event data according to some embodiments. FIG. 10 shows list-mode data 1010, associating each detected gamma-ray event with a detection time as well as other values which enable determination of a position of the event. Clustering component 1020 receives list mode data 1010 and operates as described above to define clusters of event data.

It will be assumed that five clusters are determined, Clusters A-E. Each of Clusters A-E is associated with a time period and spatial information as described above. The time period of Cluster A is before the time period of Cluster B, which is before the time period of Cluster C, etc. Each cluster includes a portion of list-mode data 1010 corresponding to events which occurred during the time period of the cluster.

List-mode data 1030 includes events of list-mode data 1010 which occurred during the time period associated with Cluster A. Each of data sets 1040*a-d* includes list-mode data of a respective cluster as well as a motion vector relative to the data of Cluster A. The motion vector of Cluster B may comprise a vector between spatial information of Cluster A and spatial information of Cluster B. Similarly, the motion vector of Cluster C may be determined based on (e.g., may be a sum of) the vector between the spatial information of Cluster A and the spatial information of Cluster B and a vector between the spatial information of Cluster B and spatial information of Cluster C.

Motion correction component 1050 may apply motion correction as is known in the art to convert the list-mode data of each of data sets 1040*a-d* to the frame of reference of list-mode data 1030. Conversion may be based on the motion vector of each of data sets 1040*a-d*, which may indicate relative motion with respect to the frame of reference of list-mode data 1030 as described above. Next, reconstruction component 1060 generates image 1070 based on list-mode data 1030 and the motion-corrected data sets 1040*a-d*. As is known in the art, the data may be subjected to various data processing algorithms (attenuation correction, denoising, etc.) prior to reconstruction.

According to some embodiments, motion correction is applied during reconstruction. With reference to FIG. 10, reconstruction component 1060 may generate image 1070 based on list-mode data 1030 and non-motion-corrected data sets 1040*a-d*.

Figure 11:
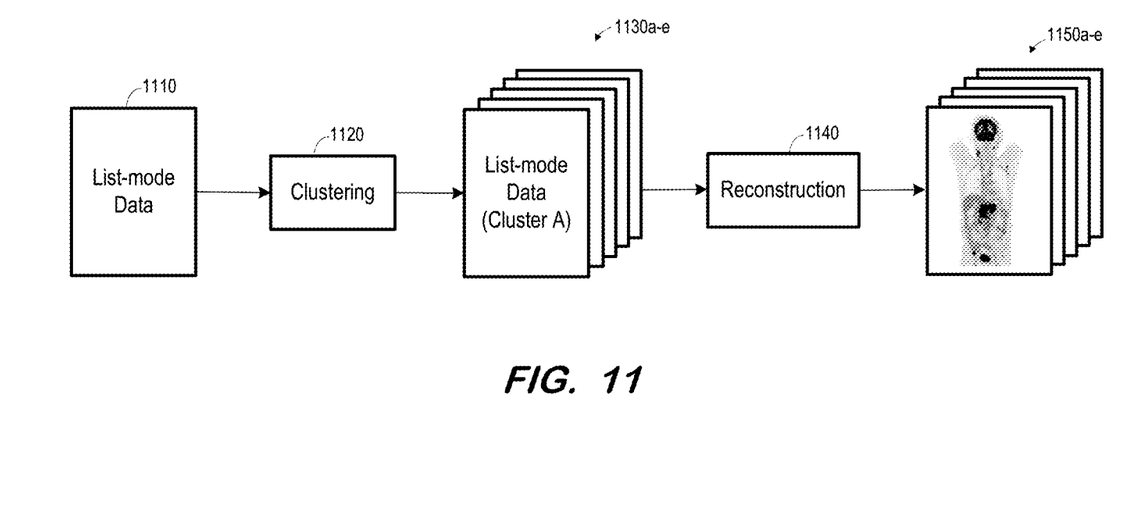
FIG. 11 illustrates a system for clustering, motion-correcting and reconstructing event data according to some embodiments.

FIG. 11 illustrates clustering and reconstructing event data according to some embodiments. Clustering component 1120 receives list mode data 1110 and operates as described above to identify event data 1130*a-e* corresponding to respective clusters.

Reconstruction component 1140 operates separately on each of event data 1130*a-e* to generate images 1150*a-e*, each of which corresponds to a respective one of event data 1130*a-e*. Accordingly, FIG. 11 illustrates generation of an image corresponding to each cluster of event data, without regard to motion vectors therebetween.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   an imaging device to:
      acquire a plurality of image data, each of the plurality of image data associated with a position and an event time;
   a processing system to:
      assign each image data to one of a plurality of bins based on the event time associated with the image data, each of the plurality of bins associated with a respective time period;
      for each bin, determine spatial information based on the positions of the image data assigned to the bin;
      identify a first pair of the plurality of bins associated with adjacent time periods;
      determine whether spatial information of one of the first pair of identified bins is within a predetermined threshold of spatial information of the other one of the first pair of identified bins;
      if the spatial information of the one of the first pair of identified bins is within the predetermined threshold of the spatial information of the other one of the first pair of identified bins:
         merge the pair of bins into a first combined bin, the first combined bin associated with a first time period corresponding to the adjacent time periods of the first pair of the plurality of bins; and
         reconstruct a first image based on the image data assigned to the first pair of the plurality of bins; and
      if the spatial information of the one of the first pair of identified bins is not within the predetermined threshold of the spatial information of the other one of the first pair of identified bins,
         reconstruct a second image based on the image data assigned to the one of the first pair of identified bins, and
         reconstruct a third image based on the image data assigned to the other one of the first pair of identified bins.

2. A system according to claim 1, the processing system to:
   identify a second pair of the plurality of bins associated with adjacent time periods;
   determine whether spatial information of one of the second pair of identified bins is within a predetermined threshold of spatial information of the other one of the second pair of identified bins; and
   if the spatial information of the one of the second pair of identified bins is within the predetermined threshold of the spatial information of the other one of the second pair of identified bins:
      merge the second pair of bins into a second combined bin, the second combined bin associated with a second time period corresponding to the adjacent time periods of the second pair of the plurality of bins; and
      reconstruct a fourth image based on the image data assigned to the second pair of the plurality of bins.

3. A system according to claim 1, the processing system to:
   identify a second pair of the plurality of bins associated with adjacent time periods;
   determine whether spatial information of one of the second pair of identified bins is within a predetermined threshold of spatial information of the other one of the second pair of identified bins;
   if the spatial information of the one of the second pair of identified bins is within the predetermined threshold of the spatial information of the other one of the second pair of identified bins, merge the second pair of bins into a second combined bin, the second combined bin associated with a second time period corresponding to the adjacent time periods of the second pair of the plurality of bins;
   determine spatial information of the first combined bin based on the positions of the image data assigned to the first plurality of bins;

determine spatial information of the second combined bin based on the positions of the image data assigned to the second plurality of bins;

if the spatial information of the first combined bin is within the predetermined threshold of the spatial information of the second combined bin, merge the image data assigned to the first plurality of bins and the image data assigned to the second plurality of bins into a third combined bin, wherein reconstruction of the first image is based on the image data assigned to the first pair of the plurality of bins and the second plurality of bins.

4. A system according to claim 1, the processing system to:

identify a second pair of the plurality of bins associated with adjacent time periods;

determine whether spatial information of one of the second pair of identified bins is within a predetermined threshold of spatial information of the other one of the second pair of identified bins;

if the spatial information of the one of the second pair of identified bins is within the predetermined threshold of the spatial information of the other one of the second pair of identified bins, merge the second pair of bins into a second combined bin, the second combined bin associated with a second time period corresponding to the adjacent time periods of the second pair of the plurality of bins;

determine spatial information of the first combined bin based on the positions of the image data assigned to the first plurality of bins;

determine spatial information of the second combined bin based on the positions of the image data assigned to the second plurality of bins;

determine a motion vector based on the spatial information of the first combined bin and the spatial information of the second combined bin; and motion-correct the image data assigned to the second plurality of bins based on the motion vector, wherein reconstruction of the first image comprises reconstruction of the first image based on the image data assigned to the first plurality of bins and the motion-corrected image data assigned to the second plurality of bins.

5. A system according to claim 1, the processing system to:

identify a third bin associated with a time period adjacent to the time period of the first combined bin;

determine whether spatial information of the third bin is within a predetermined threshold of spatial information of a first-in-time bin of the first pair of bins; and if the spatial information of the third bin is within the predetermined threshold of the spatial information of the first-in-time bin of the first pair of bins, merge the third bin into the first combined bin, wherein reconstruction of the first image comprises reconstruction of the first image based on the image data assigned to the first plurality of bins and the image data assigned to the third bin.

6. A system according to claim 5, the processing system to:

identify a second pair of the plurality of bins associated with adjacent time periods;

determine whether spatial information of one of the second pair of identified bins is within a predetermined threshold of spatial information of the other one of the second pair of identified bins;

if the spatial information of the one of the second pair of identified bins is within the predetermined threshold of the spatial information of the other one of the second pair of identified bins, merge the second pair of bins into a second combined bin, the second combined bin associated with a second time period corresponding to the adjacent time periods of the second pair of the plurality of bins;

determine spatial information of the first combined bin based on the positions of the image data assigned to the first plurality of bins and the image data assigned to the third bin;

determine spatial information of the second combined bin based on the positions of the image data assigned to the second plurality of bins;

determine a motion vector based on the spatial information of the first combined bin and the spatial information of the second combined bin; and motion-correct the image data assigned to the second plurality of bins based on the motion vector, wherein reconstruction of the first image comprises reconstruction of the first image based on the image data assigned to the first plurality of bins, the image data assigned to the third bin, and the motion-corrected image data assigned to the second plurality of bins.

7. A system according to claim 1, wherein the image data comprises list-mode positron emission tomography data, and the first image is a positron emission tomography image.

8. A method comprising:

acquiring a plurality of event data, each of the plurality of event data associated with a position and an event time;

associating each of the event data to one of a plurality of bins based on the event time associated with the event data, each of the plurality of bins associated with a respective time period;

for each bin, determining a representative position based on the positions of the event data associated with the bin;

identifying a first pair of the plurality of bins associated with adjacent time periods;

determining whether a representative position of one of the first pair of identified bins is within a predetermined threshold of a representative position of the other one of the first pair of identified bins;

if the representative position of the one of the first pair of identified bins is within the predetermined threshold of the representative position of the other one of the first pair of identified bins:

merging the pair of bins into a first combined bin, the first combined bin associated with a first time period corresponding to the adjacent time periods of the first pair of the plurality of bins; and reconstructing a first image based on the event data associated with the first pair of the plurality of bins; and if the spatial information of the one of the first pair of identified bins is not within the predetermined threshold of the spatial information of the other one of the first pair of identified bins:

reconstructing a second image based on the image data assigned to the one of the first pair of identified bins; and reconstructing a third image based on the image data assigned to the other one of the first pair of identified bins.

9. A method according to claim 8, further comprising:
identifying a second pair of the plurality of bins associated with adjacent time periods;
determining whether a representative position of one of the second pair of identified bins is within a predetermined threshold of a representative position of the other one of the second pair of identified bins; and
if the representative position of the one of the second pair of identified bins is within the predetermined threshold of the representative position of the other one of the second pair of identified bins:
  merging the second pair of bins into a second combined bin, the second combined bin associated with a second time period corresponding to the adjacent time periods of the second pair of the plurality of bins; and
  reconstructing a fourth image based on the image data associated with the second pair of the plurality of bins.

10. A method according to claim 8, further comprising:
identifying a second pair of the plurality of bins associated with adjacent time periods;
determining whether a representative position of one of the second pair of identified bins is within a predetermined threshold of a representative position of the other one of the second pair of identified bins;
if the representative position of the one of the second pair of identified bins is within the predetermined threshold of the representative position of the other one of the second pair of identified bins, merging the second pair of bins into a second combined bin, the second combined bin associated with a second time period corresponding to the adjacent time periods of the second pair of the plurality of bins;
determining a representative position of the first combined bin based on the positions of the image data associated with the first plurality of bins;
determining a representative position of the second combined bin based on the positions of the image data associated with the second plurality of bins;
if the representative position of the first combined bin is within the predetermined threshold of the representative position of the second combined bin, merging the image data associated with the first plurality of bins and the image data associated with the second plurality of bins into a third combined bin,
wherein reconstructing the first image is based on the image data associated with the first pair of the plurality of bins and the second plurality of bins.

11. A method according to claim 8, further comprising:
identifying a second pair of the plurality of bins associated with adjacent time periods;
determining whether a representative position of one of the second pair of identified bins is within a predetermined threshold of a representative position of the other one of the second pair of identified bins;
if the representative position of the one of the second pair of identified bins is within the predetermined threshold of the representative position of the other one of the second pair of identified bins, merging the second pair of bins into a second combined bin, the second combined bin associated with a second time period corresponding to the adjacent time periods of the second pair of the plurality of bins;
determining a representative position of the first combined bin based on the positions of the image data associated with the first plurality of bins;
determining a representative position of the second combined bin based on the positions of the image data associated with the second plurality of bins;
determining a motion vector based on the representative position of the first combined bin and the representative position of the second combined bin; and
motion-correcting the image data associated with the second plurality of bins based on the motion vector,
wherein reconstructing the first image comprises reconstruction of the first image based on the image data associated with the first plurality of bins and the motion-corrected image data associated with the second plurality of bins.

12. A method according to claim 8, further comprising:
identifying a third bin associated with a time period adjacent to the time period of the first cluster;
determining whether a representative position of the third bin is within a predetermined threshold of the representative position of a first-in-time bin of the first pair of bins; and
if the representative position of the third bin is within the predetermined threshold of the representative position of the first-in-time bin of the first pair of bins, merging the third bin into the first combined bin,
wherein reconstructing the first image comprises reconstruction of the first image based on the image data associated with the first plurality of bins and the image data associated with the third bin.

13. A method according to claim 12, further comprising:
identifying a second pair of the plurality of bins associated with adjacent time periods;
determining whether a representative position of one of the second pair of identified bins is within a predetermined threshold of a representative position of the other one of the second pair of identified bins;
if the representative position of the one of the second pair of identified bins is within the predetermined threshold of the representative position of the other one of the second pair of identified bins, merging the second pair of bins into a second combined bin, the second combined bin associated with a second time period corresponding to the adjacent time periods of the second pair of the plurality of bins;
determining a representative position of the first combined bin based on the positions of the image data associated with the first plurality of bins and the image data associated with the third bin;
determining a representative position of the second combined bin based on the positions of the image data associated with the second plurality of bins;
determining a motion vector based on the representative position of the first combined bin and the representative position of the second combined bin; and
motion-correcting the image data associated with the second plurality of bins based on the motion vector,
wherein reconstructing of the first image comprises reconstruction of the first image based on the image data associated with the first plurality of bins, the image data associated with the third bin, and the motion-corrected image data associated with the second plurality of bins.

14. A method according to claim 8, wherein the image data comprises list-mode positron emission tomography data, and the first image is a positron emission tomography image.

15. A method comprising:
- acquiring a plurality of imaging event data, each of the plurality of imaging event data associated with a position and an event time;
- associating each of the imaging event data to one of a plurality of bins based on the event time associated with the imaging event data, each of the plurality of bins associated with a respective time period;
- identifying a first plurality of adjacent-in-time bins in which a spatial characteristic of the imaging event data of a first-in-time bin of the first plurality of bins is within a predetermined threshold of the spatial characteristic of the imaging event data of each other of the first plurality of adjacent-in-time bins;
- associating each of the imaging event data of the identified first plurality of adjacent-in-time bins with a first combined bin associated with the time periods of the first plurality of adjacent-in-time bins;
- identifying a second plurality of adjacent-in-time bins in which the spatial characteristic of the imaging event data of a first-in-time bin of the second plurality of bins is within a predetermined threshold of the spatial characteristic of the imaging event data of each other of the second plurality of adjacent-in-time bins;
- associating each of the imaging event data of the second plurality of adjacent-in-time bins with a second combined bin associated with the time periods of the second plurality of adjacent-in-time bins;
- determining that the time periods of the first combined bin and the time periods of the second combined bin are adjacent-in-time;
- in response to the determination that the time periods of the first combined bin and the time periods of the second combined bin are adjacent-in-time, determining whether the spatial characteristic of the imaging event data of the first combined bin is within a second predetermined threshold of the spatial characteristic of the imaging event data of the second combined bin;
- if the spatial characteristic of the imaging event data of the first combined bin is within the second predetermined threshold of the spatial characteristic of the imaging event data of the second combined bin:
  - reconstructing a first image based on the imaging event data associated with the first combined bin and the second combined bin, and
- if the spatial characteristic of the imaging event data of the first combined bin is not within the second predetermined threshold of the spatial characteristic of the imaging event data of the second combined bin:
  - motion-correcting the imaging event data of the second combined bin; and
  - reconstructing an image based on the imaging event data of the first combined bin and the motion-corrected imaging event data of the second combined bin.

16. A method according to claim 15, wherein the image data comprises list-mode positron emission tomography data, and the characteristic is a center of distribution.

17. A method according to claim 15,
- wherein motion-correcting the imaging event data of the second combined bin comprises:
- determining a motion-correction parameter based on the spatial characteristic of the imaging event data of the first combined bin and the spatial characteristic of the imaging event data of the second combined bin; and
- motion-correcting the imaging event data of the second combined bin based on the motion-correction parameter.

18. A method according to claim 17, wherein the image data comprises list-mode positron emission tomography data, and the spatial characteristic is a center of distribution.

* * * * *